(12) United States Patent
Lim

(10) Patent No.: US 11,504,512 B2
(45) Date of Patent: Nov. 22, 2022

(54) METHOD OF FABRICATING MICRONEEDLE PATCHES

(71) Applicant: Chee Yen Lim, Singapore (SG)

(72) Inventor: Chee Yen Lim, Singapore (SG)

(*) Notice: Subject to any disclaimer, the term of this patent is extended or adjusted under 35 U.S.C. 154(b) by 576 days.

(21) Appl. No.: 16/491,462

(22) PCT Filed: May 10, 2017

(86) PCT No.: PCT/SG2017/050244
§ 371 (c)(1),
(2) Date: Sep. 5, 2019

(87) PCT Pub. No.: WO2018/208223
PCT Pub. Date: Nov. 15, 2018

(65) Prior Publication Data
US 2020/0030591 A1 Jan. 30, 2020

(51) Int. Cl.
| | | |
|---|---|---|
| A61M 37/00 | (2006.01) | |
| B29C 39/02 | (2006.01) | |
| B29C 39/42 | (2006.01) | |
| B29K 105/00 | (2006.01) | |
| B29L 31/00 | (2006.01) | |

(52) U.S. Cl.
CPC ....... A61M 37/0015 (2013.01); B29C 39/026 (2013.01); B29C 39/42 (2013.01); A61M 2037/0023 (2013.01); A61M 2037/0046 (2013.01); A61M 2037/0053 (2013.01); A61M 2207/10 (2013.01); B29K 2105/0035 (2013.01); B29K 2883/00 (2013.01); B29L 2031/7544 (2013.01)

(58) Field of Classification Search
CPC ............................................ A61M 2037/0053
See application file for complete search history.

(56) References Cited

U.S. PATENT DOCUMENTS

| | | | | |
|---|---|---|---|---|
| 9,320,878 B2* | 4/2016 | Jin | ............................ | A61P 3/10 |
| 9,498,524 B2* | 11/2016 | Ghartey-Tagoe | ............................ | A61M 37/0015 |
| 9,649,281 B2* | 5/2017 | Yoshida | ................ | A61K 9/0021 |
| 9,987,236 B2* | 6/2018 | Yoshida | ................. | A61K 8/735 |

(Continued)

FOREIGN PATENT DOCUMENTS

| | | | | |
|---|---|---|---|---|
| WO | WO-2015122838 A1 * | 8/2015 | .......... | A61K 9/0021 |
| WO | 2015164840 A1 | 10/2015 | | |

OTHER PUBLICATIONS

International Search Report of PCT/SG2017/050244 dated Jan. 4, 2018.

*Primary Examiner* — Benjamin A Schiffman
(74) *Attorney, Agent, or Firm* — Patshegen IP; Moshe Pinchas

(57) ABSTRACT

In the preferred embodiment, a method of making microneedles comprises i) providing a microneedle template (300) having a plurality of microneedles cavities (360) on one surface, ii) preparing a casting solution (320) comprising at least one matrix material and its solvent, iii) subjecting said microneedle template (300) to a vacuum pressure for a length of time to deprive it of air, iv) dispensing the casting solution (320) over the air-deprived microneedle template, v) allowing the casting solution (320) to be drawn into the air-deprived microneedle cavities (360) completely, and vi) allowing the dissolving microneedles to solidify or dry in a controlled environment.

17 Claims, 7 Drawing Sheets

(56) References Cited

U.S. PATENT DOCUMENTS

| | | | |
|---|---|---|---|
| 10,045,936 B2* | 8/2018 | Mochizuki | A61M 37/0015 |
| 10,195,410 B2* | 2/2019 | Jin | B29C 39/026 |
| 10,441,532 B2* | 10/2019 | Wakamatsu | A61M 37/0015 |
| 10,596,361 B2* | 3/2020 | Wakamatsu | A61M 37/00 |
| 10,828,478 B2* | 11/2020 | McAllister | A61M 37/0015 |
| 11,007,678 B2* | 5/2021 | Ogawa | C25D 1/10 |
| 11,135,413 B2* | 10/2021 | Okano | A61M 37/0015 |
| 2016/0082626 A1* | 3/2016 | Kato | B29C 43/52 425/127 |
| 2017/0050010 A1* | 2/2017 | McAllister | A61M 37/0015 |
| 2017/0057124 A1* | 3/2017 | Wakamatsu | A61K 38/385 |
| 2018/0028459 A1* | 2/2018 | Urabe | B29C 39/021 |
| 2018/0333899 A1* | 11/2018 | Francis | B29C 33/40 |
| 2020/0197679 A1* | 6/2020 | Li | B29C 45/2626 |
| 2021/0016071 A1* | 1/2021 | McAllister | B33Y 80/00 |
| 2022/0032026 A1* | 2/2022 | Kulik | A61M 37/0015 |

* cited by examiner

METHOD OF FABRICATING MICRONEEDLE PATCHES

CROSS-REFERENCE TO RELATED APPLICATION

This application is a § 371 national phase application of PCT/SG2017/050244 filed May 10, 2017 entitled "METHOD OF FABRICATING MICRONEEDLE PATCHES," the contents of which being incorporated by reference in their entirety herein.

FIELD OF THE INVENTION

The present invention relates to fabrication of microneedle patches for medical and cosmetic uses. Particularly, the present invention relates to methods of fabricating microneedle patches for medical and cosmetic uses.

BACKGROUND OF THE INVENTION

Microneedles have been around for many years. Since the first microneedle U.S. Pat. No. 3,964,482 was filed in the 1960's by Alza Corporation, many types of microneedles have been inspired and made to date. Although microneedles were first incepted in the 1960s, in nearly twenty years no microneedles were reduced into practice, probably due to non-existence of viable technology for fabricating them.

The first generation of microneedles, which were made of silicon wafers, was introduced by microfabrication techniques in the early 1990s, after the first patent expired. The advantage of this technology is that it is commonly known and practised and the disadvantages are that it takes very long to process (it relies on wet etching process, which may take one to a few weeks) and it has very limited size options. This is due to the fact that the microneedles are etched on silicon wafers, and normally the height of the microneedles is limited to below 300 um (a silicon wafer's thickness is 0.5 mm or 500 um). Using extra thick wafers will tremendously increase the material cost and the production cost (much more silicon has to be etched to form longer needles). With new technologies such as dry reactive ion etching (DRIE), the etching time may be reduced. But DRIE is not made for production use, so the maintenance costs remains high and the yield remains low.

Following the silicon microneedles, metallic, plastic and dissolving microneedles were also invented, in the 2000s. In the early days, the microfabrication technique was used extensively for making microneedles. For making metallic or plastic microneedles, a negative mould was made either directly from etching or by duplicating a silicon master mould (e.g. casting PDMS over the silicon master mould): for making metallic microneedles, the negative mould was sputtered with a conductive layer and was subjected to electroplating process to deposit metal on the negative mould. For making plastic microneedles, the negative mould was subjected to hot-embossing or other thermal moulding processes. These solid microneedles, which were made of silicon, metal and plastic materials, could carry a coating of drug on their surface so that the drug can be released to the skin after they penetrate the skin. However, the coating of drug might peel off during the penetration process if the coating was not too adhesive or it might remain on the needles' surface if the coating was too adhesive. In addition, the drug coating contains very small amount of drug and any attempt to increase the drug will inevitably increase the thickness of the coating.

For making dissolving microneedles, solvents or biodegradable materials were used. Dissolving microneedles made in the early stage faced multiple challenges including lacking the right dissolving material that was strong enough to penetrate the skin and dissolve after that; forming these materials into sharp tips, etc. are among the most challenging issues. Once all these challenges were solved, dissolving microneedles gain wide popularity in $2010s$ because of the effectiveness in drug delivery. This is explained by the fact that the drugs are encapsulated within the microneedles and will only be released after the microneedles penetrate and dissolve in the skin. Relatively, they also can carry much more drug than their solid counterpart.

U.S. Pat. No. 9,498,524B2 discloses several methods of making dissolving microneedles with a microneedle template. Essentially, the patent teaches that a microneedle template is subjected to physical compression from two sides to close up the cavities removing the air. Subsequently, a casting solution is dispended over the template and the compression is released after the dispensing to open up the cavities, allowing the solution to fill the cavities. The cast template may also be subjected to vibration or pressurization to eliminate bubbles. FIG. 1 shows schematically, how it can be performed. A microneedle template 100 is compressed side-way such that the microneedle cavities 120 were closed up purging the air out of the cavities. Then the casting solution 140 is cast over the closed-up microneedle cavities 120. Lastly, the physical compression is removed, opening up the microneedle cavities 120 and creating a vacuum in the cavities to draw in the casting solution. It is hard to ensure that all air is purged during the physical compression, and repeated compressions will damage and shorten the life of the microneedle templates.

In addition, the patent also discloses the use of vacuum for filling the cavities of the microneedle template. For example, a microneedle template which is cast with solution may be placed in a vacuum chamber. The lower ambient pressure will make the bubbles in the cavities expand and rise to the surface of the solution and burst when the vacuum is released. FIG. 2 shows a schematic diagram of the process: a microneedle template 200 is subjected to vacuuming to reduce the air in the microneedle cavities 220, after which the casting solution 240 is cast over the microneedle cavities under the same vacuum pressure. In theory, there is no air in the microneedle cavities 220 and the casting solution can freely flow into and fill up the cavities. It is found that operating in vacuum pressure imposes great difficulty in manufacturing setting, and that the low vacuum pressure will cause the air in the casting solution 240 to expand and form more bubbles 260 when the casting solution 240 is cast.

Another vacuum method that the patent discloses is a method which subjects the microneedle template to vacuum pressure followed by casting the solution is over the template while it is in the vacuum chamber. The vacuum reduces the air in the cavities and upon releasing the vacuum; the solution will flow into the cavities. Pressurization may be used to further speed up the filling after the vacuum pressure is released. FIG. 3 explains the process as follows: A microneedle template 300 is cast over with a casting solution 320 and subjected to vacuum pressure. The vacuum above the casting solution 320 creates a negative pressure difference between the vacuum and the bubbles 340 trapped in the microneedle cavities 360, which in turn makes the bubbles expand and rise to the surface of the casting solution 320, and finally burst in vacuum. It is found that more than often the casting solution is too viscous and thick to allow all the bubbles pass through it before bursting in vacuum. As a conclusion, the filling methods reported in the prior arts are imperfect for a mass production method.

PCT application WO2015/164840A1 further discloses several filling methods which make use of pressure difference during the filling process. For example, the filling methods involve applying positive pressure on top of the microneedle template, applying suction (vacuum) pressure on the bottom of the microneedle template, or applying a positive pressure on top and a negative pressure on the bottom of the microneedle template during a filling step.

There are several disadvantages associated with these filling methods. First of all, for the physical compression method, the physical compression may damage the microneedle templates due to accelerated physical wear and tear and the process is disruptive to the dispensing and filling processes. Secondly, for the vacuuming method, it imposes great inconvenience to cast a solution over a microneedle template in a vacuum chamber. Thirdly, and most importantly, all of these methods do not ensure 100% elimination of bubbles. For example, the physical compression may not fully close up all cavities and therefore some air will still reside and cause bubbles to generate. For the vacuuming method, whether before or after the solution is cast over the microneedle template, the casting solution, which is too thick or too viscous, acts like a blanket insulating the cavities and bubbles from the vacuum pressure; so not all the bubbles will neither expand nor surface up but remain in the cavities. This thick blanket effect applies also to the pressurization and vibration method. In short, these disclosed methods are not optimal or effective in providing high yield of dissolving microneedle patches. Lastly and most importantly, the vacuum pressure may induce bubble formation within the casting solution, which cannot be eliminated by the vacuum pressure itself.

PCT application WO2015/122838A1 discloses a method of using centrifugal force to remove the bubbles in the cavities. While this centrifugation method is very effective in removing bubbles in the cavities, it lacks the industrial scale for mass production because every microneedle template has to be placed in and out of a centrifuge, limiting the production efficiency. Such method has also limitation in making big patches because big patches require large volume of casting solution, and the vast volume of liquid tends to spill during centrifugation process.

It is therefore clear that there is a long-felt need for an industrially scalable but yet simple and effective method for filling up the cavities in the microneedle templates. The present invention proposes a solution to this long-felt need.

SUMMARY OF THE INVENTION

Fabrication of dissolving microneedles requires three elements, namely providing a microneedle template, preparing a casting solution, and filling up the microneedle cavities with the casting solution. As explained in the following paragraphs, the microneedle template defines the tip size, the edge sharpness and the surface roughness of the dissolving microneedles; the casting solution dictates the strength and the dissolving ability of the dissolving microneedles; and the filling process determines the quality and the yield of the production of dissolving microneedles.

A microneedle template is essentially a mould comprising a plurality of negative moulding cavities, or hereinafter "microneedle cavities". The microneedle templates are normally moulded from a master mould of microneedles. On the other hand, the casting solution is made up of at least one dissolving material which, when moulded into microneedles and hardened, provides sufficient strength for penetrating the skin and yet is "weak" enough to dissolve or degrade in the skin after the penetration. The casting solution may contain one or more dissolving materials or other substances including at least one active pharmaceutical ingredient. The Microneedle templates and the casting solution are consumed in the production of dissolving microneedles, and they are the two major costs in the production.

Lastly, the filling of the casting solution into the microneedle cavities is the only process involved in the dissolving microneedles production line. It involves a dispensing step wherein the casting solution is dispensed over the air-deprived microneedle template, a filling step wherein the casting solution is allowed to be drawn into the microneedle cavities and fill them completely, and a drying step wherein the dissolving microneedles are allowed to dry in a controlled environment.

The present invention aims to provide an effective solution for making dissolving microneedles. In the preferred embodiment, a method of making microneedles comprises i) providing a microneedle template having a plurality of microneedles cavities on one surface, ii) preparing a casting solution comprising at least one matrix material and its solvent, iii) subjecting said microneedle template to a vacuum pressure for a length of time to make the microneedle template air-deprived, iv) dispensing the casting solution over the air-deprived microneedle template, v) allowing the casting solution to be drawn into the air-deprived microneedle cavities completely, and vi) allowing the dissolving microneedles to solidify or dry in a controlled environment.

DETAILED DESCRIPTION OF THE INVENTION

The following description specifies the essential principles of the fabrication method for dissolving microneedles, and these principles are not limited in their literal meanings and should be extended to the broadest scopes as perceived and understood by a skilled man or woman in the art. "The dissolving microneedles" in this context include any microneedle with length of 10 um-3 mm having the ability to dissolve or degrade or disintegrate when they are in contact with a body; but they exclude any solid microneedles which are not dissolving naturally, i.e. made of materials such as metal, ceramic and plastics. "The microneedle master moulds" are solid, rigid and non-dissolving moulds comprising microneedle patterns that can be duplicated onto a microneedle template as negative patterns of microneedles, or cavities. "The microneedle templates" in this context means secondary moulds comprising a plurality of microneedle cavities; and they are normally duplicated from a microneedle master mould. "The microneedle cavities" is referred to the negative patterns on a microneedle template that are duplicated exactly from a microneedle master mould. "The casting solution" includes a solution containing at least a matrix material and its solvent and any active pharmaceutical ingredients. "Atmospheric conditions" means a range of temperatures and pressures under indoor conditions, for example 15° C. to 25° C. and atmospheric pressure of 1 bar. "Air-deprived" means in a state of lacking air due to removal of air from the pores in the bulk material.

The making of dissolving microneedles comprises three steps, namely providing a microneedle template comprising a plurality of microneedle cavities, preparing a casting solution, and filling the casting solution into microneedle cavities.

(a) Fabrication of Microneedle Templates

Figure 1:
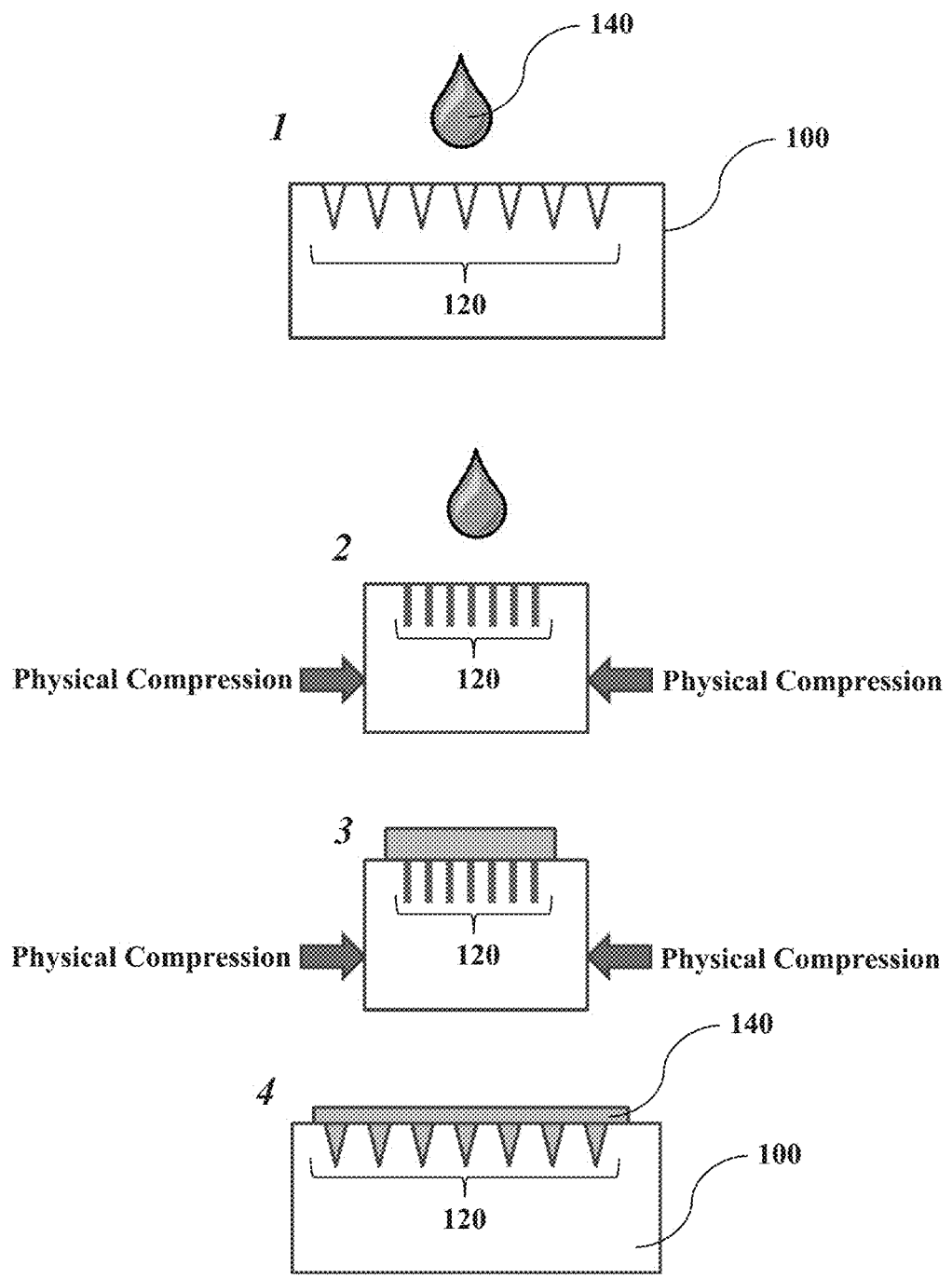
FIG. 1 shows a prior art involving compressing a microneedle template to close up the microneedle cavities, casting a solution over the closed cavities, and releasing the compression thus opening up the cavities to draw in the solution
Figure 2:
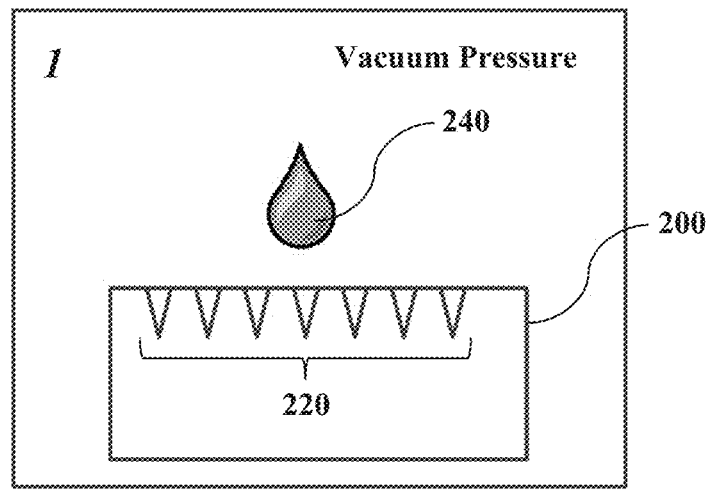
FIG. 2 shows a prior art involving vacuuming a microneedle template, casting a solution over the template, and releasing the vacuum thus expanding and bursting the bubbles in the cavities.
Figure 2:
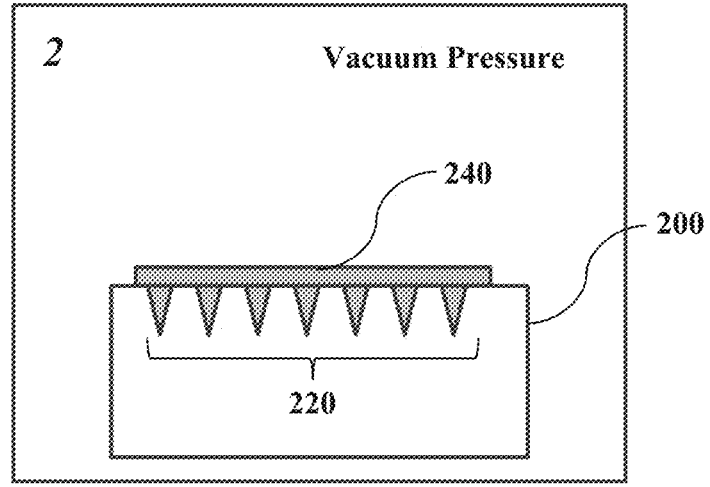
Figure 3:
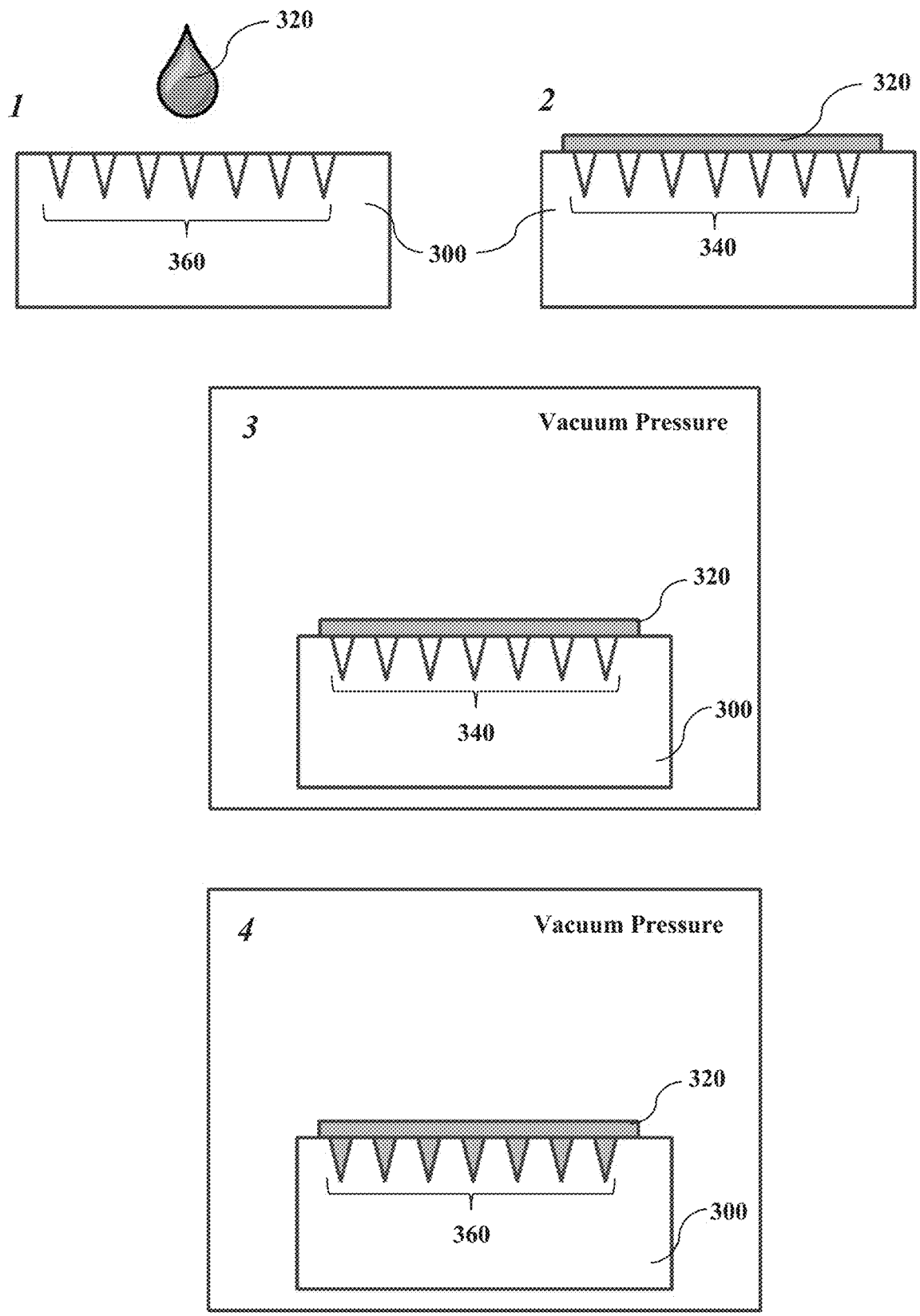
FIG. 3 shows a prior art involving casting a solution over a microneedle template, subjecting the cast template to vacuum pressure thus expanding and bursting the bubbles in the cavities.
Figure 4:
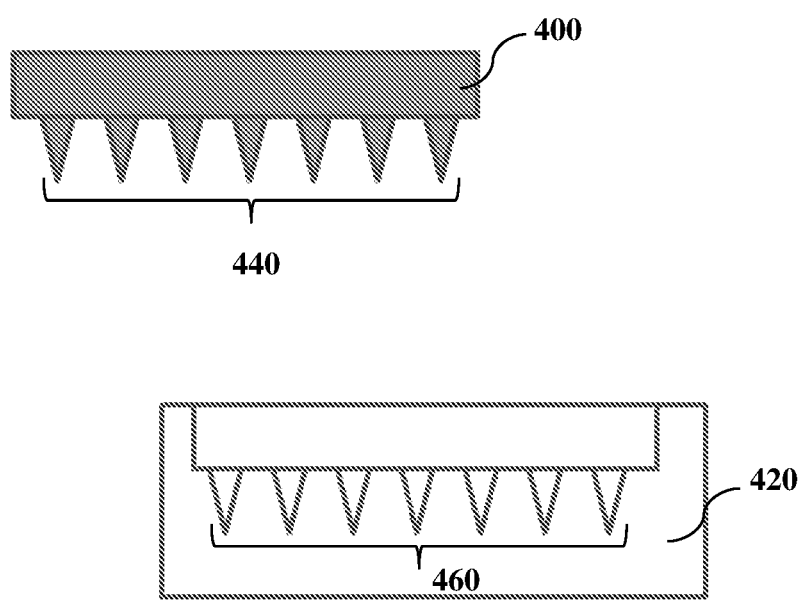
FIG. 4 shows a microneedle master mould and a microneedle template which comprises a plurality of microneedle cavities on one surface.

As mentioned earlier, the microneedle template defines the tip size, the edge sharpness and the surface roughness of the dissolving microneedles. A good quality microneedle template is a prerequisite of premium-grade dissolving microneedles. The fabrication of microneedle templates involves moulding a material on a microneedle master mould. The microneedle master mould can be obtained by microfabrication method, precision machining including laser machining, electro-discharge machining, grinding, milling, etc. which form a plurality of microneedles, or the positive patterns. Subsequently, this master mould will be used to duplicate a microneedle template which contains an exact but opposite pattern of the master moulds, i.e. inheriting the microneedles' shape and forming microneedle cavities. FIG. 4 shows a microneedle master mould 400 and a duplicated microneedle template 420. The master mould 400 comprises a plurality of microneedles 440 on one surface and the duplicated microneedle template 420 comprises a plurality of microneedle cavities 460 which are the exact but opposite patterns of the microneedles 440 on the master mould. The master mould normally is made of metal such as stainless steel, but it may also be made of silicon if it is worked via microfabrication method, or other materials such as plastic or ceramic materials.

One key criterion for choosing the material for making the microneedle template 420 is the air permeability of the material, i.e. the material has the ability to allow air, but not liquid, to go through the bulk material. One key property of such material is that its pores are isolated and not inter-connected with one another. Inter-connected pores will make the material porous which is permeable to both gas and liquid. Hence, these isolated pores in the template are normally filled with air and when the template is subjected to vacuum pressure, the air in the pores will be sucked out, making the template in an air deprived state. As explained later, this air-deprived state of the microneedle templates is the key feature in the present invention.

Due to the requirements of de-moulding the microneedles after they solidify, the microneedle templates also have to be reasonably soft, flexible and elastic. One candidate which possesses all these characteristics is the silicone elastomer, or poly-dimethyl-siloxane (PDMS). It was discovered in this work that PDMS elastomer exhibited air permeability that led to the air-deprival feature when subjected to a vacuum pressure, which filled up the microneedle cavities completely. This property can be analogous to an electrical capacity in an electrical circuit, where electrical charges are stored and discharge from the capacity. The air-deprived microneedle templates are also analogous to a squeezed sponge that tries to replenish its air once it is released. The microneedle cavities had the dimensions of 600 um height, 200 um×200 um base, and pyramidal shape. The methods of duplicating microneedle templates from microneedle master moulds include direct casting, compression moulding and LSR (liquid silicone rubber) injection moulding.

(b) Preparation of the Casting Solution

The performance of the dissolving microneedles is essentially their ability to penetrate the skin effectively and then dissolve at a desirable rate. A casting solution is the root of the dissolving microneedles' performance. The preparation of the casting solution is relatively straightforward. It involves at least a matrix material and probably at least one active pharmaceutical ingredient. Please note that the matrix material can also be the active pharmaceutical ingredient and in this case there is only the matrix material in the casting solution. The matrix material is made of but not limiting to sugars, hydrogels and biomaterials that are typically bio-compatible, bio-degradable, namely sodium hyaluronate (more commonly known as hyaluronic acid HA), polyvinylpyrrolidone PVP, carboxymethyl cellulose CMC, polyethylene glycol diacrylate PEGDA, etc. with various molecular weights. These matrix materials' solvent is water. Appropriate amount of the matrix material is dissolved in a solvent to form a casting solution with certain concentration, such as 0.01 g/ml-1 g/ml, after which the active pharmaceutical ingredient(s) if any will be added into the casting solution and stir thoroughly to make a homogeneous solution. The casting solution may be subjected to continuous stirring, degassing, refrigerating etc. so that it is in optimal condition for casting later. For example, to make a HA casting solution, 0.6 g of sodium hyaluronate of molecular weight<10 kDa is dissolved in 1 ml of distilled water by centrifuging. Subsequently, this casting solution can be loaded with an active pharmaceutical ingredient with a desirable concentration.

(c) Filling of the Casting Solution into the Microneedle Cavities

Figure 5:
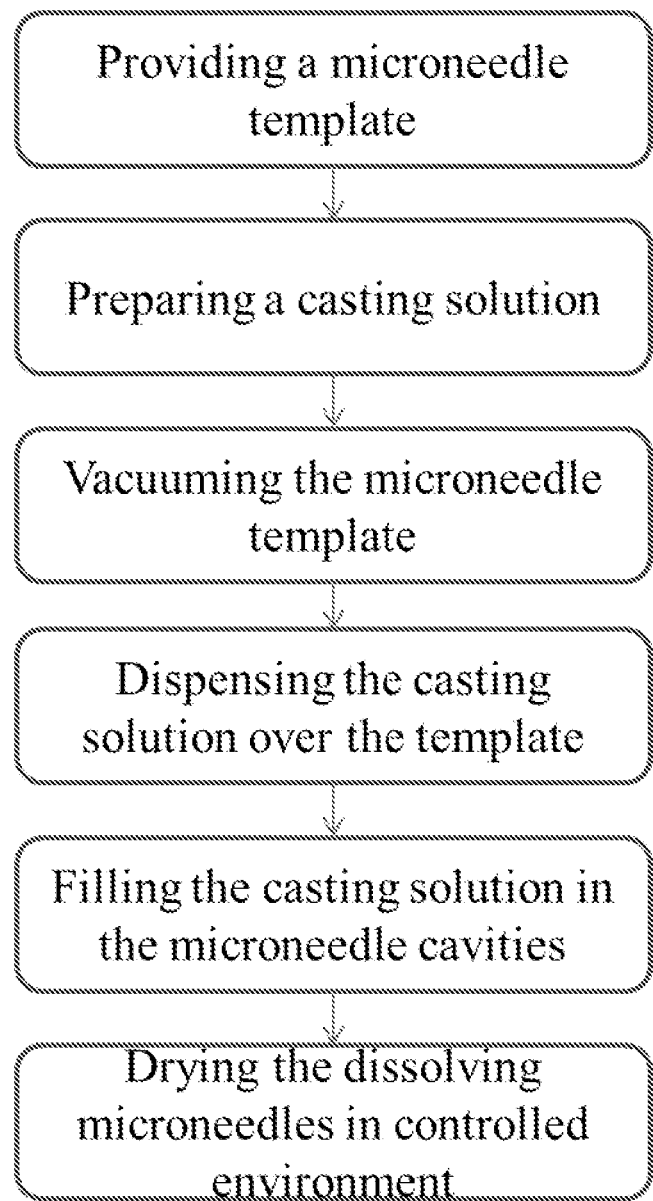
FIG. 5 shows the preferred embodiment's process flow in making dissolving microneedles.

Cavity-filling is the sole key process in the making of dissolving microneedles in the production line. This process will determine the quality and yield of the production. Filling the microneedle cavities with the casting solution is the last and key step in the production of dissolving microneedles. It involves a vacuuming step for depriving the microneedle template of air, a dispensing step wherein the casting solution is dispensed over the air-deprived microneedle template, a filling step wherein the casting solution is allowed to be drawn into the microneedle cavities and fill them completely, and a drying step wherein the dissolving microneedles are allowed to dry in a controlled environment. Now the following paragraphs will describe the preferred embodiment of the present invention. FIG. 5 shows a process flow chart of the preferred embodiment. Firstly, an air-permeable microneedle template is provided by moulding. Secondly, a casting solution comprising at least a matrix material and its solvent, as well as at least an active ingredient is prepared.

Thirdly, the microneedle template is subjected to vacuum pressure in a vacuum chamber for a length of time. Although it is clear, we would like to highlight that after this point the vacuum pressure is removed after the specified duration. The applied vacuum pressure can be −0.1 bar to −1.0 bar, more specifically can be −0.3 bar to −1.0 bar, and optimally can be −0.7 bar to −1.0 bar. The duration of the vacuuming is dependent on the vacuum pressure. The lower the vacuum pressure is applied to the microneedle templates, the longer duration they require for this method to work well. It was found that optimal parameters range from −0.7 bar to −1.0 bar and 1-3 minutes. It is worth noting although it is quite clear that the vacuum pressure is removed from the air-deprived microneedle templates, e.g. the air-deprived microneedle templates are taken out of the vacuum chamber for the subsequent steps. Fourthly, the microneedle template is cast with the casting solution in atmospheric conditions. It is worth noting that the atmospheric conditions are the simplest and minimum conditions for this step to work well, but slightly pressurized or vacuumed conditions may also work. The key idea is to avoid substantial vacuuming which causes the casting solution to bubble. Fifthly, a period of one-three minutes is allowed for the filling process to complete. It is also worth noting that depending on the volume and depth of the microneedle cavities, the filling time can be significantly less or more than 1-3 minutes.

Lastly, the filled microneedle template is subjected to a controlled environment so that the casting solution (i.e. the dissolving microneedles) to solidify and dry. The controlled environment provides the necessary environmental conditions for the dissolving microneedles to dry or solidify properly. According to our records, the optimal environmental conditions are as follows 1) a humidity of RH35%-RH60%, 2) a temperature range between 15° C.-30° C., 3) consisting of a steady air flow, 4) under a vacuum or pressurized environment, etc. to regulate the drying rate of the dissolving microneedles.

Figure 6:
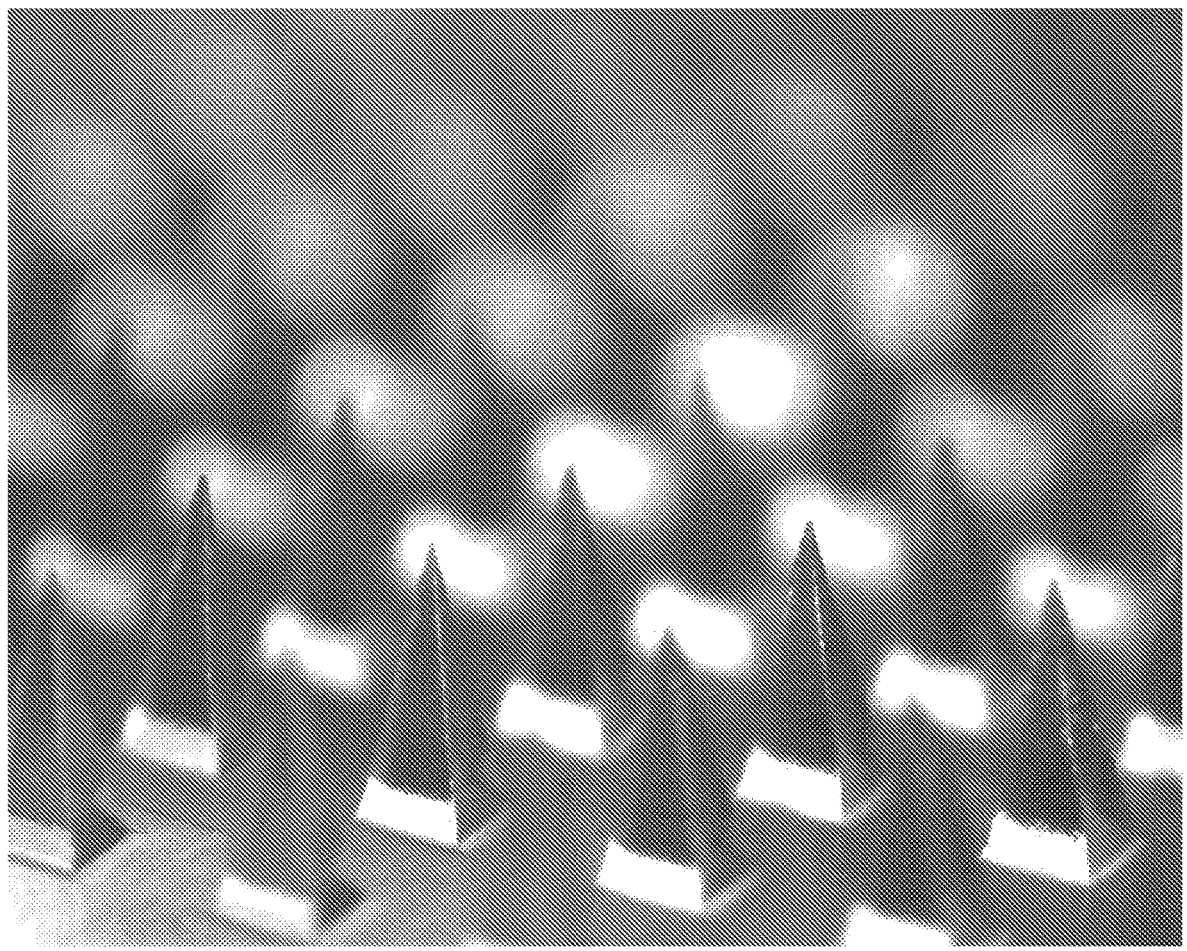
FIG. 6 shows a dissolving microneedle patch made by the preferred embodiment of the present invention.

FIG. 6 shows a dissolving microneedle patch made by the preferred embodiment. As shown in the figure, the tips are sharp (within 5 um-15 um), the edges are well defined and the surface is smooth. The process is simple and efficient, and it has been employed to make thousands of batches of dissolving microneedle patches without any failure.

Example 1

A batch of microneedle templates was made for studying the various effects of the manufacturing parameters. These microneedle templates were made by casting PDMS from Dow Corning's Sylgard 184 on stainless steel microneedle master mould. The PDMS: harder ratio used was 10:1. The microneedle configurations were: 14×14 array, Height=600 um, Base=200 um×200 um, Pitch (centre-to-centre distance) =500 um, pyramidal shape. The cast moulds were subjected to vacuum pressure for degassing, at −0.7 bar and −1.0 bar. Some specimens were left at room conditions (i.e. at 1.0 bar) as the control specimens. The degassed specimens were then subjected to heat curing at 80° C. for 20 minutes (Specimens A to G) and some were left at room conditions for 8 hours (control specimens I, J and K). Subsequently, a casting solution was prepared by adding sodium hyaluronate (HA) in distilled water at the concentration of 0.6 g/ml. The mixture was rigorously stirred and was subjected to centrifuging of 2 kRPM for 1 minute to ensure total dissolution of HA in water. The microneedle templates were subjected vacuuming at −0.7 bar and −1.0 bar for 3 minutes before the casting solution was cast over the microneedle cavities. An optical microscope with 200× was used to observe the filling process for determining the filling time.

Figure 7:
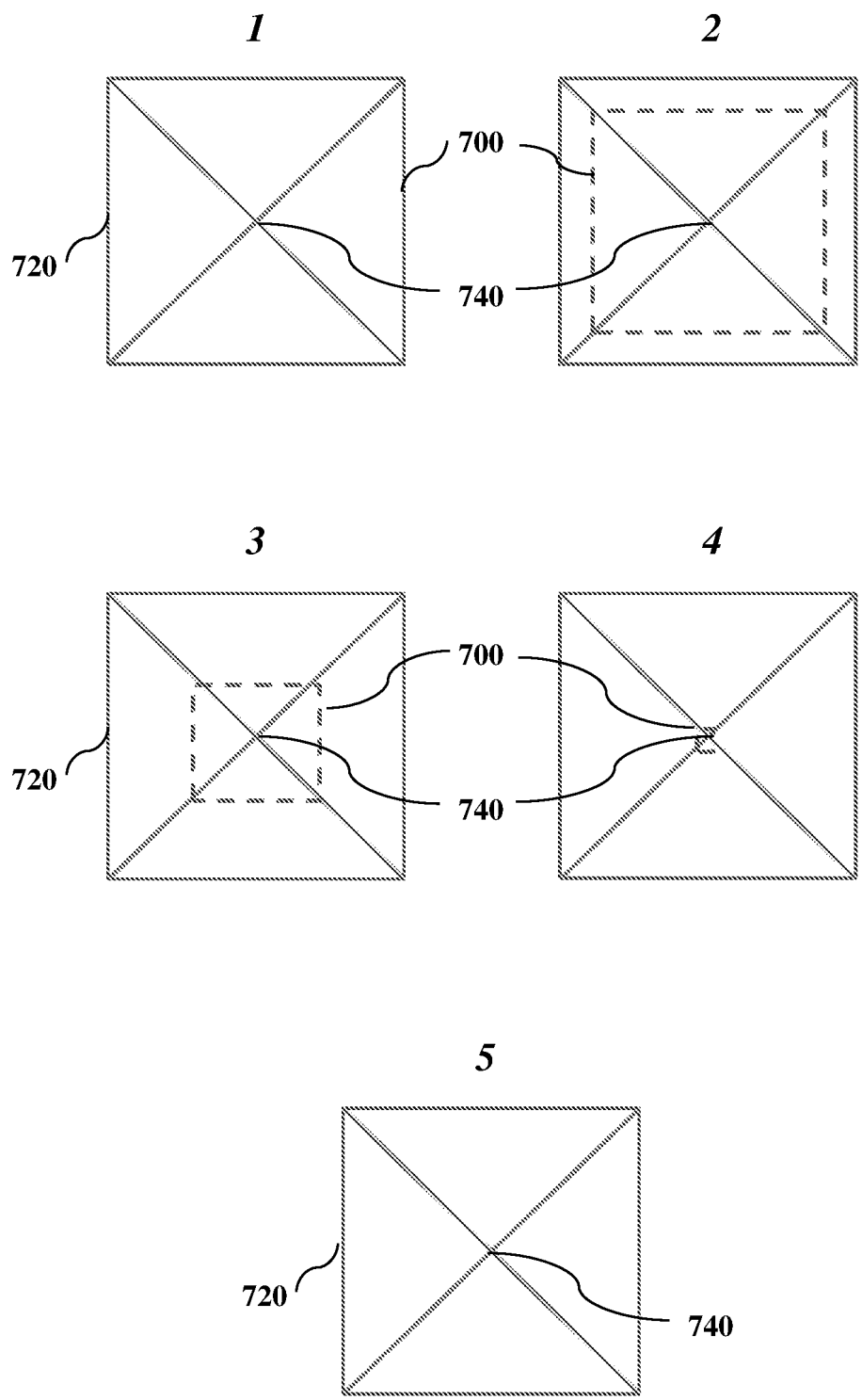
FIG. 7 shows a schematic representation of the filling process, showing the movement of the solution front towards the tip of the cavity.

FIG. 7 shows a schematic representation of the filling process, showing the movement of the solution's liquid front towards the tip of the cavity. As shown in the figure, the liquid front 700 is at the base of the cavity 720 initially and progresses towards to tip 740 (bottom) of the cavity 720. When the cavity 720 is completely filled, the liquid front 700 will disappear. Table 1 below summarizes the specimens' configurations and their respective filling times.

TABLE 1

| Specimen | Thickness | Heat Curing | Vacuum Pres (bar) | Vacuum Time (s) | Duration (s) |
| --- | --- | --- | --- | --- | --- |
| A | 4 mm | Yes | −0.7 | 180 | 138 |
| B | 4 mm | Yes | −1.0 | 180 | 73 |
| C | 4 mm | Yes | −0.7 | 180 | 156 |
| D | 4 mm | Yes | −0.7 | 180 | 160 |
| E | 6 mm | Yes | −0.7 | 180 | 176 |
| F | 6 mm | Yes | −1.0 | 600 | 61 |
| G | 6 mm | Yes | −1.0 | 180 | 108 |
| H | 4 mm | No | −0.7 | 180 | 165 |
| I | 4 mm | No | −1.0 | 180 | 93 |
| J | 4 mm | No | −0.7 | 180 | 136 |
| K | 4 mm | No | −1.0 | 180 | 85 |

Specimens A and B shows that by increasing the vacuum pressure from −0.7 bar to −1.0 bar, the filling time was reduced from 138 sec to 73 sec, or 47% reduction. Similarly, by comparing specimens F and G, the filling time was reduced from 108 sec to 61 sec if the vacuuming duration was increased from 180 sec to 600 sec. This phenomenon can be explained by the fact that when the microneedle templates are subjected to vacuum pressure, the air in the pores of the bulk templates will be sucked out of the bulk material. The greater the suction, or the longer the suction is applied to the templates, the more air will be removed from the microneedle templates. Once the suction is removed, the microneedle templates are turned into a very air-deprived state and therefore they will be vigorously drawing in air to fill its pores. When the casting solution is cast over the microneedle cavities, it covers the microneedle cavities and form air bubbles in each cavity. As the PDMS template takes in the air in the cavities to fill its pores (in the vicinity of the microneedle cavities), the casting solution is drawn into the cavities and fills them up completely.

By comparing specimens A to H and B to I, we found that the heat curing improved the filling times 16% and 21% respectively. This phenomenon can be explained by the fact that the heat during the curing expands the bubbles in the liquid PDMS, increasing the pores size and making the templates more air-permeable thereby reducing the filling times.

By comparing specimens A and E, we found that the thickness will have a negative effect on the filling time, i.e. when the thickness was increased from 4 mm to 6 mm, the filling time was increased from 138 sec to 176 sec, or 27% increase.

What is claimed is:

1. A method of making dissolving microneedles, the method comprising:
   a. providing a microneedle template comprising a plurality of microneedle cavities wherein the microneedle template is air permeable,
   b. subjecting the microneedle template to a vacuum pressure and depriving the microneedle template of air,
   c. preparing a casting solution comprising at least one matrix material and its solvent, and
   d. removing the vacuum pressure and dispensing the casting solution over the microneedle cavities in the air-deprived microneedle template under atmospheric conditions.

2. A method of making dissolving microneedles in claim 1, wherein the microneedle template is made of an air-permeable elastomer.

3. A method of making dissolving microneedles in claim 1, wherein the microneedle template is made of polydimethylsiloxane.

4. A method of making dissolving microneedles in claim 1, wherein the casting solution further comprising at least one active pharmaceutical ingredient.

5. A method of making dissolving microneedles in claim 1, wherein the matrix material is selected from the group consisting of sodium hyaluronate and polyvinylpyrrolidone.

6. A method of making dissolving microneedles in claim 5, wherein the solvent for the matrix material is water.

7. A method of making dissolving microneedles in claim 1, wherein the matrix material is selected from the group consisting of sodium hyaluronate, polyvinylpyrrolidone, polyethylene glycol diacrylate and carboxymethyl cellulose.

8. A method of making dissolving microneedles in claim 1, wherein the vacuum pressure subjected to the microneedle template is at least −0.3 bar to at least −1.0 bar relative to atmospheric pressure.

9. A method of making dissolving microneedles in claim 1, wherein the vacuum pressure subjected to the microneedle template is at least −0.7 bar to at least −1.0 bar relative to atmospheric pressure.

10. A method of making dissolving microneedles in claim 1, wherein the duration for subjecting the microneedle template to a vacuum pressure is at least 1- to at least 3 minutes.

11. A method of making dissolving microneedles in claim 1, further comprising
   a. a filling step wherein a length of time is allowed immediately after the dispensing step for the casting solution to fill up the microneedle cavities completely, and
   b. a drying step wherein the filled microneedle template is placed in a controlled environment for a length of time to allow the dissolvable microneedles to solidify or dry.

12. A method of making dissolving microneedles in claim 11, wherein the duration of the filling step is at least 1- to at least 3 minutes.

13. A method of making dissolving microneedles in claim 11, wherein the controlled environment for the drying step has a temperature range of 15° C.-30° C.

14. A method of making dissolving microneedles in claim 11, wherein the controlled environment for the drying step has a relative humidity of RH35%-RH65%.

15. A method of making dissolving microneedles in claim 11, wherein the controlled environment for the drying step has a steady air flow.

16. A method of making dissolving microneedles in claim 11, wherein the controlled environment for the drying step is under vacuum conditions.

17. A method of making dissolving microneedles in claim 11, wherein the controlled environment for the drying is under pressurized conditions.

* * * * *